US010471084B2

(12) United States Patent
McConnell et al.

(10) Patent No.: US 10,471,084 B2
(45) Date of Patent: Nov. 12, 2019

(54) COMPOSITION AND METHOD FOR TREATING ACUTE RESPIRATORY TRACT INFECTIONS

(71) Applicant: Glycom A/S, Kongens Lyngby (DK)

(72) Inventors: Bruce McConnell, La Tour de Peilz (CH); Louise Kristine Vigsnæs, København (DK)

(73) Assignee: Glycom A/S, Hørsholm (DK)

( * ) Notice: Subject to any disclaimer, the term of this patent is extended or adjusted under 35 U.S.C. 154(b) by 0 days.

(21) Appl. No.: 15/555,936

(22) PCT Filed: Mar. 4, 2016

(86) PCT No.: PCT/DK2016/050062
§ 371 (c)(1),
(2) Date: Sep. 5, 2017

(87) PCT Pub. No.: WO2016/138911
PCT Pub. Date: Sep. 9, 2016

(65) Prior Publication Data
US 2018/0036327 A1 Feb. 8, 2018

(30) Foreign Application Priority Data

Mar. 5, 2015 (DK) ................................ 2015 70124
Feb. 24, 2016 (DK) ................................ 2016 70097

(51) Int. Cl.
*A61K 31/7048* (2006.01)
*A61K 31/702* (2006.01)
*A61K 9/20* (2006.01)
*A23L 33/125* (2016.01)

(52) U.S. Cl.
CPC ........ *A61K 31/7048* (2013.01); *A23L 33/125* (2016.08); *A61K 9/205* (2013.01); *A61K 9/2054* (2013.01); *A61K 31/702* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2012/0172319 A1* | 7/2012 | Chow | A23L 33/40 514/21.92 |
| 2012/0172331 A1 | 7/2012 | Buck et al. | |
| 2015/0031645 A1 | 1/2015 | Buck et al. | |

FOREIGN PATENT DOCUMENTS

| | | |
|---|---|---|
| EP | 2465509 A1 | 6/2012 |
| TW | 201244721 A1 | 11/2012 |
| WO | 2009077352 A1 | 6/2009 |
| WO | 2010115934 A1 | 10/2010 |
| WO | 2010115935 A1 | 10/2010 |
| WO | 2011008086 A1 | 1/2011 |
| WO | 2011008087 A1 | 1/2011 |
| WO | 2011100980 A1 | 8/2011 |
| WO | 2012076323 A1 | 6/2012 |
| WO | 2012092158 A1 | 7/2012 |
| WO | 2012155916 A1 | 11/2012 |
| WO | 2013044928 A1 | 4/2013 |
| WO | 2013091660 A1 | 6/2013 |
| WO | 2014100696 A1 | 6/2014 |

OTHER PUBLICATIONS

Melville, Frontiers in Neuroscience, May 2013, vol. 7, Article 79, pp. 1-9.*
Intermountain Healthcare, Caring for Your Late Preterm Baby, Fact Sheet for Patients and Families, internet article, 2009-2014.*
Carlos C. Grijalva et al., "Antibiotic Prescription Rates for Acute Respiratory Tract Infections in US Ambulatory Settings", JAMA, vol. 302, No. 7, Aug. 19, 2009, American Medical Association, pp. 758-766.
L. Renee Ruhaak et al., "Detection of milk oligosaccharides in plasma of infants", Anal Bioanal Chem, Jul. 25, 2014, pp. 5775-5784.
Frnacesca Bottacini et al., "Diversity, ecology and intestinal function of bifidobacteria", Microbial Cell Factories, Aug. 31-Sep. 4, 2014, pp. 1-15.
Sabrina Duranti et al., "Exploration of the Genomic Diversity and Core Genome of the Bifidobacterium adolescentis Phylogenetic Group by Means of a Polyphasic Approach", AEM Jornal, vol. 79, No. 1, Jan. 2013, pp. 336-346.
Geralyn Duska-McEwen et al. "Human Milk Oligosaccharides Enhance Innate Immunity to Respiratory Syncytial Virus and Influenza in Vitro" Scientific Research, Food and Nutrition Sciences, Aug. 2014, pp. 1-14.
S. Asakuma et al., "Variation of major neutral oligosaccharides levels in human colostrum", European Journal of Clinical Nutrition, Mar. 21, 2007, pp. 488-494.
"Supplementary European Search Report", dated Sep. 10, 2018, pp. 1-8.

* cited by examiner

*Primary Examiner* — Layla D Berry
(74) *Attorney, Agent, or Firm* — Kunzler Bean & Adamson

(57) ABSTRACT

A composition and method for using it to prevent and/or relieve symptoms of acute respiratory tract infections, particularly bronchitis, in immune-compromised persons, particularly adults. The composition contains 2'-fucosyllactose and lacto-N-neotetraose and/or lacto-N-tetraose.

18 Claims, No Drawings

COMPOSITION AND METHOD FOR TREATING ACUTE RESPIRATORY TRACT INFECTIONS

FIELD OF THE INVENTION

This invention relates to a composition for use in preventing an acute respiratory tract infection (ARI) and/or relieving symptoms of an ARI in immune-compromised persons, particularly adults. The invention also relates to a method for the treatment or prevention of an ARI in immune-compromised persons.

BACKGROUND OF THE INVENTION

Acute infections of the respiratory tract are very common, especially in infants, children and the elderly. In the US, for patients five years or older, ARI's accounted for 8% of all visits to primary care and 58% of all antibiotics prescribed in primary care (Grijalva et al. *JAMA* 302, 758 (2009)). These infections produce conditions such as otitis, bronchitis, pneumonia, sinusitis, pharyngitis and strep throat.

Acute bronchitis, which results from an infection, is an inflammation of the bronchi. It is one of the most prevalent respiratory infections treated in primary care and occurs most often during the winter. It is an acute illness usually lasting less than three weeks with coughing as the main symptom and at least one other lower respiratory tract symptom such as wheezing, sputum production or chest pain. Older people can have symptoms such as confusion or rapid breathing. About 90% of cases of acute bronchitis are caused by viruses, such as rhinoviruses, coronaviruses, adenoviruses, metapneumoviruses, parainfluenza viruses, respiratory syncytial viruses and influenza viruses. About 10% of cases are caused by bacteria such as *Mycoplasma pneumoniae, Chlamydophila pneumoniae, Bordetella pertussis, Streptococcus pneumonia* and *Haemophilus influenzae*.

Treatment for acute bronchitis usually involves just treating the symptoms, e.g., with non-steroidal anti-inflammatory drugs (NSAIDs) to treat fever and sore throat. As most cases of acute bronchitis are caused by viruses, antibiotics are not recommended but tend to be heavily overused. Over 60% of bronchitis patients are prescribed antibiotics, and this is a leading cause of the development of antibiotic-resistant bacteria. This over prescription occurs despite fact that there is no clinical benefit for most patients.

While acute bronchitis is generally not serious, serious complications can occur as a result. Pneumonia is the most common complication of acute bronchitis and occurs when the infection spreads further into the lungs, causing air sacs inside the lungs to fill up with fluid. 1 in 20 cases of acute bronchitis leads to pneumonia. Another possible complication is respiratory failure. It is also possible that acute bronchitis can lead to chronic bronchitis. These complications are more common in immune-compromised people such as the elderly, diabetics, etc. For example, the number of hospitalisations for acute lower respiratory infections in England is about three times higher in those over 75 years than in younger people. Further, the average length of stay for acute respiratory conditions increases progressively with age.

Although most ARI's are resolved reasonably quickly, the suffering and the financial costs of respiratory tract infections are enormous. Little effective prevention is currently possible outside of two strategies: attempting to avoid contact with or spreading of infectious agents; and vaccination for influenza and pneumococcal pneumonia.

Human milk oligosaccharides (HMOs) have been proposed as a possible means for preventing or treating ARIs. In WO 2012/076323, a method is disclosed for preventing or treating ARIs in children of up to three years old using HMOs. The children are treated using nutritional compositions which contain an N-acetyl lactosamine, a sialylated oligosaccharide and a fucosylated oligosaccharide. The method is in particularly suited for treating otitis or bronchiolitis. In WO 2014/100696, a nutritional composition is disclosed for modulating inflammation, such as a respiratory virus-induced inflammation, in adults and the elderly. In US 2015/0031645, a method is disclosed for improving the immune system's response to a viral infection, such as a respiratory viral infection, in children of up to twelve years old. A nutritional composition which contains 2'-fucosyllactose and lacto-N-neotetraose is disclosed as being preferred.

However, there remains a need for an effective, as well as convenient and safe, method for preventing ARI infections and/or relieving their symptoms in immune-compromised persons, particularly adults.

SUMMARY OF THE INVENTION

This invention provides a composition for use in preventing and/or relieving symptoms of an acute respiratory tract infection (ARI) in immune-compromised persons, particularly adults, more particularly pregnant women and the elderly, the composition comprising 2'-fucosyllactose (2'-FL) and lacto-N-neotetraose (LNnT) and/or lacto-N-tetraose (LNT).

Advantageously, the composition consists essentially of 2'-FL and LNnT and/or LNT. More advantageously, the composition contains more 2'-FL than LNnT and/or LNT. Even more advantageously, the mass ratio of 2'-FL to LNnT and/or LNT in the composition is about 1.5 to about 4.5. In one embodiment, the mass ratio of 2'-FL to LNnT and/or LNT in the composition is about 1.5 to about 2.5, for example about 2:1. In another embodiment, the mass ratio of 2'-FL to LNnT and/or LNT in the composition is about 3.5 to about 4.5, for example about 4:1.

Also advantageously, the composition comprises at least 0.5 g of 2'-FL and LNnT and/or LNT, more advantageously at least 1 g of 2'-FL and LNnT and/or LNT, for example about 1.5 g or more of 2'-FL and LNnT and/or LNT.

Also advantageously, the composition is a once-a-day formulation providing at least about 2 g of 2'-FL and LNnT and/or LNT per day, more advantageously at least 3 g of 2'-FL and LNnT and/or LNT.

This invention further provides a method of preventing acute respiratory tract infection and/or relieving symptoms of acute respiratory tract infection in immune-compromised persons, particularly adults, more particularly pregnant women and the elderly, the method comprising administering, to the person, an effective dose of 2'-FL and LNnT and/or LNT.

Advantageously, the dose of 2'-FL and LNnT and/or LNT is administered prophylactically to the person on a daily basis to the immune-compromised person. More advantageously, the dose is administered prophylactically in periods of higher risk, for example during winter.

Also advantageously, the person is administered a daily dose of at least 0.5 g of 2'-FL and LNnT and/or LNT, more advantageously at least 1 g of 2'-FL and LNnT and/or LNT, for example about 1.5 g or more of 2'-FL and LNnT and/or LNT. More adavantageously, the person is administered the 2'-FL and LNnT and/or LNT in a single daily dose of at least about 2 g of 2'-FL and LNnT and/or LNT per day, even more advantageously at least 1 3 g of 2'-FL and LNnT and/or LNT.

Also advantageously, the abundance of bifidobacteria in the intestine of the person is increased by the dose of 2'-FL and LNnT and/or LNT, more advantageously a bifidobacterium of the B. adolescentis phylogenetic group, especially B. adolescentis and/or B. pseudocatenulatum.

Surprisingly, 2'-FL and LNnT and/or LNT are particularly effective in preventing ARI and/or relieving symptoms of ARI, and in particular preventing and/or relieving symptoms of bronchitis in immune-compromised persons.

DETAILED DESCRIPTION OF THE INVENTION

The following terms preferably have the following meanings:

"Immune-compromised" means that the immune system of a person, particularly an adult, is significantly weakened or absent. Examples of immune-compromised people are HIV and AIDS patients, patients undergoing chemotherapy or radiation therapy for cancer, patients having certain cancers and genetic disorders, pregnant women, and the elderly. Immune-compromised people can also be those who cannot or should not take pharmaceutical medications against infections, such as pregnant women.

"Elderly" means a person of age 60 or above.

"Adult" means a person above age 13.

"Preventing ARI" means the prevention and the reduction of frequency and/or occurrence and/or severity and/or duration of ARI. Occurrence is related to the number of any ARI. Frequency is related to the number of the same ARI.

"Relieving symptoms of ARI" means reducing the symptoms of ARI, and in particular reducing fever, easing the breathing process and/or diminishing the pain and/or easing sleep.

"Nutritional composition" means a composition which nourishes a person. A nutritional composition is usually taken orally or enterally and usually includes one or more macronutrients, such as lipids, fats, and proteins, and one or more micronutrients.

"Probiotic" means a microbial cell preparation or components of microbial cells with a beneficial effect on the health or well-being of the host (Salminen et al. *Trends Food Sci. Technol.* 10, 107 (1999)).

"Bifidobacteria of the *B. adolescentis* phylogenetic group" is meant a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)).

The invention is based upon the surprising finding that a combination of 2'-fucosyllactose (2'-FL) and lacto-N-neotetraose (LNnT) and/or lacto-N-tetraose (LNT) is effective to protect immune-compromised persons, particularly adults, against ARI and/or relieve symptoms of ARI. 2'-FL and LNnT and/or LNT are oligosaccharides found in human breast milk and safe for long-term consumption. Therefore, the combination is particularly suitable for protecting pregnant women and the elderly where reduced drug intake is advisable.

The 2'-FL and LNnT and/or LNT can be produced by well-known processes using microbial fermentation, enzymatic processes, chemical syntheses, or combinations of these technologies. As examples, using chemistry, LNnT can be made as described in WO 2011/100980 and WO 2013/044928, LNT can be synthesized as described in WO 2012/155916 and WO 2013/044928, a mixture of LNT and LNnT can be made as described in WO 2013/091660, and 2'-FL can be made as described in WO 2010/115934 and WO 2010/115935.

To obtain the benefits of preventing ARI and/or relieving symptoms of ARI, the immune-compromised person is administered a composition containing, preferably consisting essentially of, 2'-FL and LNnT and/or LNT. The composition can be in any suitable form, such as, for example, a nutritional composition, a nutritional supplement, a drink, a food, a medical device or a pharmaceutical. The supplement, medical device or pharmaceutical can be in a galenic form such as a tablet, capsule, pastille, powder in a sachet or a liquid.

The composition of the invention is preferably a synthetic composition. The term "synthetic composition" designates a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition of the invention typically comprises 2'-FL and LNnT and/or LNT, and in some embodiments may comprise one or more compounds or components other than 2'-FL and LNnT and/or LNT that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. According to one embodiments, the composition of the invention can be co-administered to a person along with a vaccine, preferably an influenza vaccine. Some non-limiting embodiments of a synthetic composition of the invention are also described below.

Nutritional Compositions

A suitable nutritional composition can contain a source of protein, lipids and/or digestible carbohydrates and can be in powdered, liquid or solid form. The composition can be formulated to be the sole source of nutrition or as a nutritional supplement.

Suitable protein sources include milk proteins, soy protein, rice protein, pea protein and oat protein, or mixtures of these. Milk proteins can be in the form of milk protein concentrates, milk protein isolates, whey protein or casein, or mixtures of these. The protein can be a whole protein or a hydrolysed protein, either partially hydrolysed or extensively hydrolysed. The protein can also be provided in the form of free amino acids. The protein can comprise about 5% to about 30% of the energy of the nutritional composition, normally about 10% to 20%.

The protein source can be a source of glutamine and/or cysteine. The glutamine source can be a glutamine dipeptide and/or a glutamine enriched protein. Glutamine can be included due to its use by enterocytes as an energy source. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures of these. Generally, digestible carbohydrates provide about 35% to about 55% of the energy of the nutritional composition. Preferably, the nutritional composition is low in or free from lactose. A particularly suitable digestible carbohydrate is a low dextrose equivalent (DE) maltodextrin.

Suitable lipids include medium chain triglycerides (MCT) and long chain triglycerides (LCT). Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. Generally the lipids provide about 35% to about 50% of the energy of the nutritional composition. The lipids can include polyunsaturated fatty acids such as omega-6 and omega-3 fatty acids. Preferably, polyunsaturated fatty acids provide less than about 30% of total energy of the lipid source. Decreasing the levels of polyunsaturated fatty acids is believed to decrease sensitivity to peroxidation which can be beneficial for persons having inflammatory conditions.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron. For example, the composition can contain per daily dose one or more of the following micronutrients in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can further comprise at least one probiotic bacterial strain. Suitable probiotic bacterial strains include *Lactobacillus rhamnosus* ATCC 53103, *Lactobacillus rhamnosus* CGMCC 1.3724, *Lactobacillus paracasei* CNCM 1-21 16, *Lactobacillus reuteri, Lactobacillus johnsonii* CN CM 1-1225, *Streptococcus salivarius* DSM 13084, *Bifidobacterium lactis* CNCM 1-3446, *Bifidobacterium longum* ATCC BAA-999, *bifidobacterium breve, Bifidobacterium infantis*. Preferably, the nutritional composition contains from 10e3 to 10e12 cfu of the probiotic bacterial strain per g of composition on a dry weight basis, more preferably between 10e7 and 10e12 cfu.

If necessary, the nutritional composition can contain emulsifiers and stabilisers such as soy, lecithin, citric acid esters of mono- and di-glycerides, and the like.

The nutritional composition can also contain other substances which can have a beneficial effect such as lactoferrin, nucleotides, nucleosides, and the like.

For liquid applications, the nutritional composition can be in the form of a reconstitutable powder, a liquid concentrate, or a ready-to-use formulation. In liquid form, the nutritional composition can be fed to a person via a nasogastric tube or by having the person drink it. Various flavours, fibres and other additives can also be present.

The nutritional composition can be prepared in any suitable manner. For example, it can be prepared by blending together the protein, the digestible carbohydrate source, and the fat source in appropriate proportions. If used, the emulsifiers can be included at this point. The vitamins and minerals can be added at this point but are usually added later to avoid thermal degradation. Any lipophilic vitamins, emulsifiers and the like can be dissolved into the fat source prior to blending. Water, preferably water which has been subjected to reverse osmosis, can then be mixed in to form a liquid mixture. The temperature of the water is conveniently in the range between about 50° C. and about 80° C. to aid dispersal of the ingredients. Commercially available liquefiers can be used to form the liquid mixture. The 2'-FL and LNnT and/or LNT are added at this stage if the final product will be in liquid form. If the final product is to be a powder, the oligosaccharides can be added at this stage if desired. The liquid mixture is then homogenised, for example in two stages.

The liquid mixture can then be thermally treated to reduce bacterial loads, by rapidly heating the liquid mixture to a temperature in the range between about 80° C. and about 150° C. for a duration between about 5 seconds and about 5 minutes, for example. This can be carried out by means of steam injection, an autoclave or a heat exchanger, for example a plate heat exchanger.

Then, the liquid mixture can be cooled to between about 60° C. and about 85° C. for example by flash cooling. The liquid mixture can then be again homogenised, for example in two stages between about 10 MPa and about 30 MPa in the first stage and between about 2 MPa and about 10 MPa in the second stage. The homogenised mixture can then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The 2'-FL and LNnT and/or LNT can be added at this stage by dry-mixing, or by blending them in a syrup form of crystals, along with the probiotic bacterial strain(s) if used, and spray-dried (or freeze-dried).

If a liquid composition is preferred, the homogenised mixture can be sterilised then aseptically filled into suitable containers or can be first filled into the containers and then retorted.

When the nutritional product is a ready-to-feed nutritional liquid, the total concentration of 2'-FL and LNnT and/or LNT in the liquid, by weight of the liquid, is from about 0.02% to about 2.0%, including from about 0.03% to about 1.5%, including from about 0.04% to about 1.0%. When the nutritional product is a concentrated nutritional liquid, the total concentration of HMOs in the liquid, by weight of the liquid, is from about 0.04% to about 4.0%, including from about 0.06% to about 3.0%, including from about 0.08% to about 2.0%.

The nutritional composition can also be formulated into solid and semi-solid forms such as cereal bars, yoghurts and the like.

Galenic Forms

The synthetic composition can also be in a galenic form such as a capsule, tablet or sachet. For example, the composition can be in a tablet form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethylcellulose (HPMC), sodium carboxymethylcellulose, polyhydroxyethylmethylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQ10") and glutathione. The unit dosage forms, especially those in sachet form, can also include various nutrients including macronutrients.

The galenic forms can fall within any suitable regulatory framework, for example they can be nutritional supplements, foods for special medical purposes/medical foods, medical devices or drugs.

Administration Dosing

For preventing acute respiratory tract infections (ARI) and/or relieving symptoms of ARI in immune-compromised person, preferably an adult, the amount of 2'-fucosyllactose and lacto-N-neotetraose and/or lacto-N-tetraose required to be administered to the adult will vary depending upon factors such as the severity of the immune deficiency, the age of the person, the form of the composition, and other medications being administered to the person. However, the required amount can be readily set by a medical practitioner and would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. An appropriate dose can be determined based on several factors, including, for example, the body weight and/or condition of the person being treated, the severity of the immune deficiency, other ailments and/or diseases of the person, and the manner of administration. Appropriate dose regimes can be determined by methods known to those skilled in the art.

The composition can be co-administered to a person along with a vaccine. Co-administration includes the administration of the composition from three months before the vaccination period to three months after the vaccination period. Suitable vaccines include a vaccine against influenza.

EXAMPLE 1

An aged mouse model is used to assess the HMO impact on the immune system of an immune-compromised individual. Ageing is associated with a noted decline in cell-mediated immune response concomitant with an increased humoral immune dysfunction. Ageing is furthermore often associated with a status of low-grade inflammation and of increased oxidative stress. Consequently, many elderly are at increased risk of infectious and non-infectious diseases that contribute to morbidity and mortality.

Specific pathogen-free male C57BL/6J mice (4-weeks old) are housed under conventional conditions (12 hours light/dark cycle, temperature 22° C., humidity 56%) and receive water and a semisynthetic diet ad libitum. Until the age of 5 months, the mice are maintained in groups of 5 per cage and then they are individually caged. At 19 months after birth, the mice are randomised into 3 groups of 10 animals and are fed either with a control semi-synthetic diet (control group, n=10) or one of two semi-synthetic diets supplemented either with 2'-FL and LNnT in a 2:1 ratio (1.2 weight % of 2'-FL and LNnT) (treatment group 1, n=10) or with 2'-FL and LNnT in a 4:1 ratio (1.2 weight % of 2'-FL and LNnT) (treatment group 2, n=10). During the 7 weeks of trial, all mice are allowed to drink and eat ad libitum.

On day 15 of the trial, the mice are immunized by subcutaneous injection (100 µl) of an inert antigen Keyhole Limpet Haemocyanin (KLH) at 100 µg in 1% Alum. Seven days after immunization, Delayed-Type Hypersensitivity (DTH) responses are elicited by injecting the recall-antigen KLH (10 µl of 0.5 µg/ml) into each mouse's right ear. The left ears are injected with vehicle alone (saline=PBS) and serve as internal controls for each animal. At 24 hours post-elicitation, and during the following 5 days, both the non-elicited (left ear) and the elicited ears (right ear) are measured. DTH responses are expressed as the magnitude of ear swelling, i.e. the change in ear thickness using the following formula: Δ in ear thickness=[elicited ear (right) ear sickness−non-elicited (left) ear sickness], where Δ in ear thickness=[post-elicitation−pre-elicitation ear thickness].

Mice are euthanized on day 42 of trial. The expression of genes involved in inflammatory processes are determined in the liver of the mice. At the autopsy, the liver is removed and a piece is immediately frozen in liquid nitrogen and then stored at −80 ° C. until further analysis.

Liver samples are transferred into 1 ml of RNA lysis buffer and homogenized using a Ribolyzer. RNA is extracted using a commercially available kit. RNA is quantified a Ribogreen RNA Quantitation Kit, and RNA quality is assayed using Agilent RNA 6000 Nano LabChip Kit. Total RNA (2 µg) is reverse transcribed using Multischbe reverse transcriptase following manufacturer's instructions. Custom-made low density arrays (LDA) with TaqMan probes are used. Gene expression is calculated using the relative quantification method ΔΔCt method with SDS 2.2.2 software (Applied Biosystems). Data are analysed by means +/−SEM and the Student's T test (unpaired) or two-way ANOVA when appropriate. Probability values of less than 5% were considered as significant.

For both treatment groups, dietary supplementation with 2'-FL and LNnT (1.2 weight % incorporated in the diet) improves cell-mediated immune response in aged mice. This supplementation alleviates age-related low-grade inflammation and oxidative damage, as observed by increased expression of genes encoding for an anti-inflammatory molecule (TGF-β2) or for molecules involved in the defence against oxidative damage (HO-1 and SOD2).

EXAMPLE 2

A total of 30 of elderly male and female persons are recruited to participate in the study. The persons are residents of long-term care facilities for the elderly. After a screening visit and run-in period of 1-2 weeks, the persons are selected. The selected individuals are randomized into two groups, each of 15 individuals, with one group consuming the treatment product and one group the placebo product for 12 weeks. The treatment product contains 2 grams of a combination of 2'-FL, and LNnT in a 2:1 mass ratio. The control product contains 2 grams glucose. Both products are in powder form in a unit dosage container.

The selected individuals are eligible to participate if they are able and willing to understand and comply with the study procedures. Individuals are excluded if: they have: participated in a clinical study one month prior to screening visit; they have abnormal results in the screening tests which are clinically relevant for study participation; they are suffering for a severe disease; they have used highly dosed probiotic supplements (yoghurt allowed) for 3 months prior to the study; they have consumed antibiotic drugs 3 months prior to the study; they have consumed on a regular basis any medication that might interfere with symptom evaluation 2 weeks prior to the study; or they are pregnant or lactating.

At the screening visit, medical history and concomitant medication is registered and a blood sample for safety analyses is collected from each selected individual. A faecal sample kit is distributed. The selected individuals are instructed to keep their samples in the freezer until the next visit.

At the second visit, eligibility criteria are checked and eligible subjects are randomised to the two arms in the trial. The faecal samples are collected and equipment for new samples are distributed. Blood samples are collected for biomarker studies.

The serum from the blood samples is transferred to cryotubes and stored at −80° C. The blood is analysed for biomarkers of safety and inflammatory response.

The faecal samples are stored at −80 ° C. until analysis. Faecal samples are subjected to 16 S RNA sequencing analysis.

The study runs for 12 weeks over the winter months with the subjects consuming either a placebo or a treatment product daily. Subjects are instructed to consume the products in the morning with breakfast.

At the end of the study, each subject has an exit visit with the medical team. Faecal samples and blood samples are collected and analysed as before.

The treatment subjects have reduced incidence of lower respiratory tract infections, particularly bronchitis. Further, incidences of fever and antibiotic use are lower in the treatment group subjects. Also, the treatment group subjects who are infected, have less acute symptoms and recover more quickly. The blood biomarker analysis indicates that the treatment subjects have improved immune status. The faecal analysis indicates that the treatment subjects have improved levels of beneficial bifidobacteria, in particular a bifidobacterium of the *B. adolescentis* phylogenetic group, especially *Bifidobacterium adolescentis* and/or *Bifidobacterium pseudocatenulatum*.

EXAMPLE 3—Nutritional Composition

A ready to feed nutritional composition is prepared from water, maltodextrin, whey protein (from cows milk), medium chain triglycerides (from coconut and/or palm kernel oil), cornstarch, soybean oil, soy lecithin, 2'-FL, LNnT, magnesium chloride, calcium phosphate, guar gum, sodium ascorbate, potassium citrate, sodium phosphate, calcium citrate, choline chloride, potassium chloride, sodium citrate, magnesium oxide, taurine, L-carnitine, alpha-tocopheryl acetate, zinc sulphate, ferrous sulphate, niacinamide, calcium pantothenate, vitamin A palmitate, citric acid, manganese sulphate, pyridoxine hydrochloride, vitamin D3, copper sulphate, thiamine mononitrate, riboflavin, beta carotene, folic acid, biotin, potassium iodide, chromium chloride, sodium selenate, sodium molybdate, phytonadione, vitamin B12.

The composition has a calorific density of 1.0 kcal/ml with a caloric distribution (% of kcal) as follows: protein: 16%, carbohydrate: 51%, fat: 33%. The protein source has an NPC:N ratio of 131:1. The MCT:LCT ratio is 70:30 and the n6:n3 ratio is 7.4:1. The osmolality (mOsm/kg water) is 270 when unflavoured. The composition contains 85% water and 1500 ml meets 100% of the RDI for 22 key micronutrients.

EXAMPLE 4—Tablet Composition

A tablet is prepared from 2'-FL, LNnT, hydroxypropyl methylcellulose, sodium alginate, gum, microcrystalline cellulose, colloidal silicon dioxide, and magnesium stearate. All raw materials except the magnesium stearate are placed into a high shear granulator and premixed. Water is sprayed onto the premix while continuing to mix at 300 rpm. The granulate is transferred to a fluidised bed drier and dried at 75° C. The dried powder is sieved and sized using a mill. The resulting powder is then lubricated with magnesium stearate and pressed into tablets. The tablets each contain 325 mg of 2'-FL and LNnT. The tablets each have a weight of 750 mg.

EXAMPLE 5—Capsule Composition

A capsule is prepared by filling about 1 g of 2'-FL and LNnT into a 000 gelatine capsule using a filing machine. The capsules are then closed. The 2'-FL and LNnT are in free flowing, powder form.

EXAMPLE 6—Capsule Composition

A capsule is prepared by filling about 1 g of 2'-FL and LNT into a 000 gelatine capsule using a filing machine. The capsules are then closed. The 2'-FL and LNnT are in free flowing, powder form.

The invention claimed is:

1. A method of at least one of preventing acute lower respiratory tract infection and relieving symptoms of acute lower respiratory tract infection in an adult whose immune system is absent or weakened due to a condition selected from the group consisting of human immunodeficiency virus infection (HIV), acquired immune deficiency syndrome (AIDS), chemotherapy for cancer, radiation therapy for cancer, cancer, genetic disorder, pregnancy, contraindication for anti-infection pharmaceutical medications ("immune-compromised person"), the method comprising administering to the immune-compromised person an effective dose of a composition consisting essentially of 2'-FL and at least one of LNnT and LNT, wherein the abundance of at least one of *Bifidobacterium adolescentis* and *Bifidobacterium pseudocatenulatum* in the intestine of the person is increased by the dose of 2'-FL and at least one of LNnT and LNT.

2. The method of claim 1 wherein the dose is administered prophylactically on a daily basis to the immune-compromised person.

3. The method of claim 1 wherein the dose is administered prophylactically to the immune-compromised person during winter.

4. The method of claim 1 wherein the person is administered a daily dose of 2'-FL and at least one of LNnT and LNT, the total dose being in the range of from about 200 mg to about 20 g.

5. The method of claim 4 wherein the person is administered the 2'-FL and at least one of LNnT and LNT in a single daily dose of from about 0.5 g to about 1.5 g or more.

6. The method of claim 4 wherein the person is administered the 2'-FL and at least one of LNnT and LNT in a single daily dose of from about 1.5 g to about 3 g or more.

7. The method of claim 4 wherein the daily dose is in the range of : 0.5 g to 1.0 g, 1.0 g to 1.5 g, 1.5 g to 2.0 g, 2.0 g to 2.5 g, 2.5 g to 3.0 g, 3.0 g to 3.5 g, 3.5 g to 4.0 g, 4.0 g to 4.5 g, or 4.5 to 5.0 g.

8. The method of claim 4 wherein the person is administered a daily dose of 2'-FL and at least one of LNnT and LNT, the total dose being in the range of from about 1 g to about 10 g.

9. The method of claim 4 wherein the person is administered a daily dose of 2'-FL and at least one of LNnT and LNT, the total dose being at least 2 g.

10. The method of claim 4 wherein the person is administered a daily dose of 2'-FL and at least one of LNnT and LNT, the total dose being at least 3 g.

11. The method of claim 4 wherein the person is administered the 2'-FL and at least one of LNnT and LNT in at least one daily dose of from about 0.5 g to about 1.5 g.

12. The method of claim 4 wherein the person is administered the 2'-FL and at least one of LNnT and LNT in a at least one daily dose of from about 1.5 g to about 3 g.

13. The method of claim 4 wherein the person is administered the 2'-FL and at least one of LNnT and LNT in at least one daily dose of from 2 g to 5 g.

14. The method of claim 4 wherein the person is administered the 2'-FL and at least one of LNnT and LNT in a at least one daily dose of from 3 g to 5 g.

15. The method of claim 1 wherein the acute lower respiratory tract infection is selected from the group consisting of acute bronchitis and pneumonia.

16. A method of preventing acute lower respiratory tract infection in an elderly adult who is not suffering from a disease and who has not consumed antibiotic drugs in the last 3 months, the method comprising daily administering to the elderly adult an effective dose of a composition consisting essentially of 2'-FL and LNnT, wherein the abundance of at least one of *Bifidobacterium adolescentis* and *Bifidobacterium pseudocatenulatum* in the intestine of the person is increased by the dose of 2'-FL and LNnT.

17. The method of claim 16, wherein administering the 2'-FL and LNnT and LNT comprises co-administering the composition with a vaccination.

18. A method of at least one of preventing acute bronchitis and pneumonia in a pregnant woman less than 60 years old, the method comprising daily administering to the pregnant woman an effective dose of a composition consisting essentially of 2'-FL and at least one of LNT and LNnT, wherein the abundance of at least one of *Bifidobacterium adolescentis* and *Bifidobacterium pseudocatenulatum* in the intestine of the person is increased by the dose of 2'-FL and at least one of LNnT and LNT.

* * * * *